(12) United States Patent
Park et al.

(10) Patent No.: US 11,667,961 B2
(45) Date of Patent: Jun. 6, 2023

(54) INTERCALATING FLUORESCENT DYES FOR LABELLING NUCLEIC ACIDS AND PREPARATION METHOD THEREOF

(71) Applicant: Bioacts Corporation, Incheon (KR)

(72) Inventors: Jin Woo Park, Incheon (KR); Ho Young Si, Incheon (KR); Eunae Jeong, Incheon (KR); Hyung Jun Yoon, Incheon (KR); Su Jung Jang, Siheung (KR)

( * ) Notice: Subject to any disclaimer, the term of this patent is extended or adjusted under 35 U.S.C. 154(b) by 216 days.

(21) Appl. No.: 17/128,012

(22) Filed: Dec. 19, 2020

(65) Prior Publication Data
US 2021/0198729 A1    Jul. 1, 2021

(51) Int. Cl.
| | | |
|---|---|---|
| *C12Q 1/68* | (2018.01) | |
| *C09B 23/06* | (2006.01) | |
| *C12Q 1/6848* | (2018.01) | |
| *C12Q 1/686* | (2018.01) | |
| *G01N 33/58* | (2006.01) | |

(52) U.S. Cl.
CPC ............ *C12Q 1/6848* (2013.01); *C09B 23/06* (2013.01); *C12Q 1/686* (2013.01); *G01N 33/582* (2013.01)

(58) Field of Classification Search
CPC ....... C09B 23/04; C09B 23/06; C09B 23/146; C12Q 1/6848; C12Q 1/686; G01N 33/582
See application file for complete search history.

*Primary Examiner* — Jezia Riley

(57) ABSTRACT

The novel intercalating fluorescent compounds of exemplary embodiments of the present invention for analyzing nucleic acids, etc. have excellent intercalating efficiency with nucleic acids such as DNA and RNA of biomaterials, and may not only continuously maintain fluorescence properties and efficiency, but also have excellent effects even in terms of storage stability such as temperature and moisture, etc. and biosafety. In addition, the fluorescent compounds have various advantages capable of being dissolved in distilled water, which is a solvent harmless to the human body, and being applied to a wide range of analysis without being limited to the analysis of specific cells and living tissues.

13 Claims, 20 Drawing Sheets

FIG. 3

| Well | Flour | Cq |
|---|---|---|
| Compound 8 | SYBR | - |
| Compound 9 | SYBR | - |
| Compound 10 | SYBR | - |
| Compound 15 | SYBR | 25.52 |
| Compound 16 | SYBR | 18.66 |
| Compound 17 | SYBR | - |

FIG. 6

| Well | Flour | Cq |
|---|---|---|
| Reference material 1 | SYBR | 20.92 |
| Reference material 2 | SYBR | 18.54 |
| Compound 16 | SYBR | 18.86 |

| Reference material 1 | | |
|---|---|---|
| Template | Flour | Cq |
| 50 ng/μl | SYBR | 20.92 |
| 5 ng/μl | SYBR | 24.07 |
| 0.5 ng/μl | SYBR | 27.34 |
| 0.05 ng/μl | SYBR | 31.03 |
| 0.005 ng/μl | SYBR | 35.26 |

(b)

| Reference material 2 | | |
|---|---|---|
| Template | Flour | Cq |
| 50 ng/μl | SYBR | 18.54 |
| 5 ng/μl | SYBR | 21.76 |
| 0.5 ng/μl | SYBR | 24.87 |
| 0.05 ng/μl | SYBR | 29.08 |
| 0.005 ng/μl | SYBR | 33.43 |

| Template | Flour | Cq |
|---|---|---|
| 50 ng/µl | SYBR | 18.86 |
| 5 ng/µl | SYBR | 22.10 |
| 0.5 ng/µl | SYBR | 25.43 |
| 0.05 ng/µl | SYBR | 29.58 |
| 0.005 ng/µl | SYBR | 33.82 |

Compound 16

| Reference material 1 | | |
|---|---|---|
| Template | Flour | Cq |
| 50 ng/μl | SYBR | 20.79 |
| 5 ng/μl | SYBR | 23.99 |
| 0.5 ng/μl | SYBR | 27.29 |
| 0.05 ng/μl | SYBR | 30.79 |
| 0.005 ng/μl | SYBR | 35.02 |

(b)

| Reference material 2 | | |
|---|---|---|
| Template | Flour | Cq |
| 50 ng/μl | SYBR | 18.98 |
| 5 ng/μl | SYBR | 22.13 |
| 0.5 ng/μl | SYBR | 25.38 |
| 0.05 ng/μl | SYBR | 29.15 |
| 0.005 ng/μl | SYBR | 33.22 |

| Compound 16 | | |
|---|---|---|
| Template | Flour | Cq |
| 50 ng/µl | SYBR | 18.75 |
| 5 ng/µl | SYBR | 22.06 |
| 0.5 ng/µl | SYBR | 25.18 |
| 0.05 ng/µl | SYBR | 29.33 |
| 0.005 ng/µl | SYBR | 33.40 |

INTERCALATING FLUORESCENT DYES FOR LABELLING NUCLEIC ACIDS AND PREPARATION METHOD THEREOF

CROSS-REFERENCE TO RELATED APPLICATIONS

This application claims priority from and the benefit of Korean Patent Application No. 10-2019-0174703, filed on Dec. 26, 2019, which is hereby incorporated by reference for all purposes as if fully set forth herein.

BACKGROUND OF THE INVENTION

Field

Exemplary embodiments of the present invention relate to an intercalating fluorescent dye that is inserted between double helical rings such as DNA and RNA of a biological material to emit fluorescence in the case of using a fluorescent compound used for analysis of cells or blood, and more particularly, to a fluorescent dye compound and a preparation method thereof using a novel intercalating mechanism with excellent stability capable of improving the binding efficiency with nucleic acids and continuously maintaining fluorescent properties and efficiency.

Description of the Related Art

Since a biomaterial itself has weak fluorescence or no fluorescence in visible and near-infrared regions, in the bio field, in order to observe biological phenomena at cellular and subcellular levels in vivo/in vitro or to make images and obtain optical images of a diseased area by being projected into the living body, imaging data have been obtained through a variety of methods using a fluorescent dye or a biocompatible material pre-labeled with a fluorescent dye in the biomaterial with optical devices.

Various optical analysis devices used in the bio field select fluorescent dyes with an excitation wavelength and an emission wavelength suitable for observing fluorescence according to embedded light sources and filters as a basic material or reagent.

Optical analysis devices mainly used include devices for research purpose, such as a fluorescence microscope for cell observation, a confocal microscope, a flow cytometer, a micro array, and a quantitative polymerase chain reaction device (qualitative PCR system), an electrophoresis device for separation and analysis of nucleic acids and proteins, a real-time in vivo imaging system, etc. In addition, devices for diagnosis and treatment, such as in vitro diagnosis devices based on nucleic acid and protein diagnostic kits (or biochips) combined with immunoassay techniques (immuno assay) or PCR analysis and statistical techniques, and operating tables and endoscopy equipment for image-guided surgery, have been known. New applications and devices with higher levels of resolution and data processing capabilities have been constantly developed.

In the selection of fluorescent dyes usable in the bio field, it is important to emit strong fluorescence when biomaterials exist in a medium, that is, an aqueous solution and an aqueous buffer, and to have excitation and fluorescence wavelengths suitable for fluorescence equipment.

In general, most of fluorescent dyes used for labeling biomaterials such as proteins or peptides include structures, such as anthranilate, 1-alkylthic isoindoles, pyrrolinones, bimanes, benzoxazole, benzimidazole, benzofurazan, naphthalenes, coumarins, cyanine, stilbenes, carbazoles, phenanthridine, anthracenes, bodipy, fluoresceins, eosins, rhodamines, pyrenes, chrysenes and acridines.

When selecting a fluorescent dye structure usable in the bio field from multiple fluorescent chromophores illustrated above, generally, it is important to emit strong fluorescence when most of biomaterials exist in a medium, that is, an aqueous solution and an aqueous buffer, and to have excitation and fluorescence wavelengths suitable for fluorescence equipment.

Dyes that may be mainly applied in the bio field should preferably have less photobleaching and quenching in aqueous or hydrophilic conditions, should have a large molecular extinction coefficient to absorb a large amount of light, should be in the visible or near-infrared region of 500 nm or more far from the fluorescence range of the biomaterial itself, and should be stable under various pH conditions. However, a structure of dyes usable for labeling biomaterials capable of satisfying the limitations is limited.

Fluorescent colorants meeting these requirements include cyanine, rhodamine, fluorescein, bodipy, coumarin, acridine, and pyrene derivatives, and may introduce a reactive group so as to be bound with a dye alone or a specific substituent in a biomolecular structure, and among them, dye compounds of xanthane-based fluorescein and rhodamine and polymethine-based cyanine derivatives are mainly commercialized.

The various fluorescent compounds described above are mainly used as markers for detecting a specific substance by using a principle of generating fluorescence or quenching by directly binding to biomaterials.

However, in embodiments of the present invention, like the dyes, the fluorescent compounds use a principle of emitting fluorescence by inserting a fluorescent compound between nucleic acid molecules having a double helix structure such as DNA and RNA without directly binding to a biomaterial.

Intercalating dyes are mainly used to receive a UV-based excitation wavelength and emit a fluorescent wavelength of 500 nm, and in order to analyze biomaterials such as blood, basically, the intercalating dyes mainly use dye compounds corresponding to an excitation wavelength of 630 nm or more and a fluorescence wavelength to be detected of 650 nm or more in consideration of problems to overcome an absorption wavelength of hemoglobin and the economical efficiency of a light source.

Dyes that are specifically bound or intercalated with nucleic acids may be used in pure solutions, cell extracts, electrophoretic gels, microarray chips, living or fixed cells, dead cells, environmental samples, etc., and may be used for detecting the presence and amount of DNA and RNA in various samples. In particular, these fluorescent dyes may be used for detection of nucleic acids through polymerase chain reaction (PCR), which is a representative method used in genomic research and medical diagnosis. At this time, in the case of general end-point PCR, since quantitative PCR in proportion to the amount of sample nucleic acids is impossible, real-time quantitative PCR (real-time PCR or qPCR) that allows quantitative analysis of the amount of nucleic acids by measuring fluorescence values that change in real time every amplification cycle has been mainly used.

A detection method using intercalating fluorescent dyes is based on DNA-binding fluorescent dyes referred to as fluorescent nucleic acid dyes or stains. Since the fluorescent nucleic acid dye consists of relatively simple molecules, there is an advantage of being relatively inexpensive due to easy designing and preparation.

As intercalating fluorescent dyes that have been widely used in the related art, there are dyes such as Sybr Green or Evagreen. When the fluorescent dyes detect nucleic acid molecules, etc., the intensity of the fluorescence signal increases in proportion to the concentration until the concentration of the fluorescent dyes reaches a reference concentration that starts to significantly inhibit the PCR process. However, thereafter, when the concentration of the dyes is further increased, the amplification of DNA decreases, so that the intensity of the observed fluorescence signal decreases, and in order to obtain a fluorescence signal with a predetermined intensity or more, a threshold cycle number needs to be increased. In addition, since the dyes are unstable under a chemical environment, there is a problem that the dye is decomposed within a few days in a buffer solution.

Therefore, in order to overcome these problems and usefully apply the dyes industrially, it is important to develop novel fluorescent dyes that have excellent optical and pH stability, have a narrow absorption and emission wavelength range in a specific wavelength range, and exhibit a high molar absorption coefficient.

SUMMARY OF THE INVENTION

Exemplary embodiments of the present invention provide a novel intercalating fluorescent compound that is mainly used for analysis using a fluorescent compound in the bio field, and the fluorescent compound of the present invention may solve the problems of conventional fluorescent compounds that the stability and fluorescence efficiency are rapidly deteriorated over time.

Conventional cyanine-based fluorescent compounds mainly used as intercalating dyes in cell analysis or nucleic acid analysis (as a representative example, Evagreen and Sybr Green are included) are fluorescent compounds mainly used to color nucleic acids in molecular biology. The fluorescent compounds bind to proteins in the serum to be selectively absorbed into the cell tissue, and emit fluorescence when irradiated with NIR or UV to analyze the transition degree and the like of a target substance in the cell tissue through an optical microscope, etc. The fluorescent compounds are preferentially inserted into double-stranded DNA and may be bound to single-stranded DNA to a low degree.

The Sybr Green compound is used to visualize DNA in gel electrophoresis, etc. and may be used for a flow cytometry and a fluorescence microscope. However, the compounds are known to be insignificant in cells, but have a possibility to cause mutations.

Therefore, exemplary embodiments of the present invention provide an intercalating fluorescent compound having excellent stability and high fluorescence efficiency in more biological and chemical environments for analysis of nucleic acids, etc., and a novel fluorescent compound provided by embodiments of the present invention may solve the problems.

One object of the present disclosure is to provide the novel intercalating fluorescent compound described above or a salt thereof.

Another object of the present disclosure is to provide a contrast agent composition for analyzing nucleic acids such as DNA and RNA including the novel intercalating fluorescent compound or a salt thereof, and a kit for detecting biomaterials to be formed by including the same.

Yet another object of the present disclosure is to provide a preparation method for preparing the novel intercalating fluorescent compound.

In order to solve the problems, exemplary embodiments of the present invention provide a novel fluorescent compound represented by the following Chemical Formula 1 or a salt thereof.

[Chemical Formula 1]

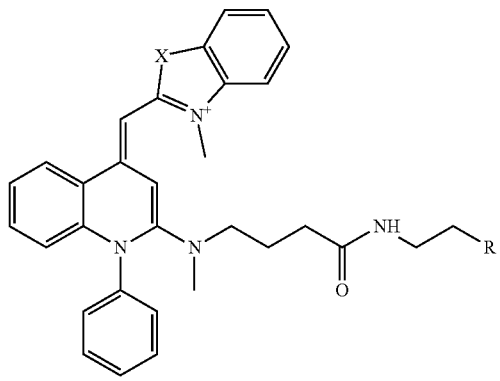

Wherein,

X is oxygen or sulfur, and

R is —SO$_2$CH(CH$_2$), —CH$_2$N(CH$_3$)$_2$, or unsubstituted alkyl having 5 to 10 carbon atoms.

The novel fluorescent compound according to embodiments of the present invention may continuously maintain fluorescence stability and fluorescence efficiency even after a long time after being labeled on a biomaterial such as DNA and RNA, and has excellent biosafety.

It was confirmed that the novel fluorescent compound according to embodiments of the present invention may exhibit excellent performance when used for observing pH changes in the body due to different optical properties according to a pH, such as exhibiting low absorption wavelength and low fluorescence wavelength intensities, exhibiting a high absorption wavelength intensity and a high fluorescence wavelength intensity at pH 7, and having a difference in absorption wavelength position. Since the pH change in the body is deeply related to phenomena such as cell proliferation, apoptosis, and muscle contraction, the fluorescent compound of embodiments of the present invention may have a large advantage of not only conducting research on cellular internalization pathways by measuring the pH change, but also observing an abnormal pH change even diseases such as cancer cells and Alzheimer's.

The fluorescent compound represented by Chemical Formula 1 above according to embodiments of the present invention has a narrower wavelength range than that of conventional intercalating dyes, exhibits a high fluorescence intensity at a low concentration, and has no cytotoxicity to be applied as an active ingredient for an in vivo imaging contrast agent capable of detecting biomaterials.

Exemplary embodiments of the present invention provide a method for labeling biomaterials comprising intercalating the fluorescent compound represented by Chemical Formula 1 above into the biomaterials.

According to embodiments of the present invention, the material to be labeled may be selected from fibers, biomaterials, nanoparticles, or organic compounds, and the biomaterial may be selected from the group consisting of proteins, peptides, carbohydrates, sugars, fats, antibodies, proteoglycans, glycoproteins and siRNA, and a preferred material to be labeled is nucleic acid molecules such as DNA and RNA.

The method for labeling the biomaterials is performed by using a buffer selected from the group consisting of a phosphate buffer, a carbonate buffer, and a tris buffer, an organic solvent selected from the group consisting of dimethyl sulfoxide, dimethylformamide, methanol, ethanol and acetonitrile, or water as a solvent and reacting the biomaterials, nanoparticles, or organic compounds with the compound of Chemical Formula 1 above at pH 5 to 12. The reaction is sufficient for 30 minutes to 48 hours at a temperature of 20° C. to 80° C.

On the other hand, in the case of the biomaterials, in most cases, the biomaterials are dissolved in a predetermined buffer from a packaging unit, and in many cases, a separate buffer or pH is required to secure the stability of the biomaterials, and as a result, it is not easy to adjust the buffer or pH with a variable. The compound of Chemical Formula 1 according to exemplary embodiments of the present invention has high stability in water-soluble conditions to be easily stored for a long time, and easily reacts with proteins under various buffers, reaction temperatures, and pH conditions to express fluorescence, so that it is suitable to be used for labeling biomaterials.

The fluorescent compounds of embodiments of the present invention for analyzing nucleic acids, etc. have excellent intercalating efficiency with nucleic acids such as DNA and RNA of biomaterials, and not only continuously maintain fluorescence properties and efficiency, but also have excellent effects even in terms of storage stability such as temperature and moisture, etc. and biosafety. In addition, the fluorescent compounds of the present invention have various effects capable of being dissolved in distilled water, which is a solvent harmless to the human body, and being applied to a wide range of analysis without being limited to the analysis of specific cells and living tissues.

BRIEF DESCRIPTION OF THE DRAWINGS

The above and other aspects, features and other advantages of the present invention will be more clearly understood from the following detailed description taken in conjunction with the accompanying drawings, in which:

FIG. 3 illustrates a $C_q$ value when DNA is synthesized using a reagent using the fluorescent compound in accordance with exemplary embodiments of the present invention;

FIG. 6 illustrates $C_q$ values when DNA is synthesized using a fluorescent compound of embodiments of the present invention and a reference material;

FIG. 9 illustrates $C_q$ values according to concentrations of a compound of embodiments of the present invention and a reference material before reaction when DNA is synthesized using the compound of embodiments of the present invention and the reference material;

FIG. 13 illustrates $C_q$ values according to concentrations of a compound of embodiments of the present invention and a reference material after reaction when DNA is synthesized using the compound of embodiments of the present invention and the reference material.

DETAILED DESCRIPTION OF THE PREFERRED EMBODIMENT

Figure 1:
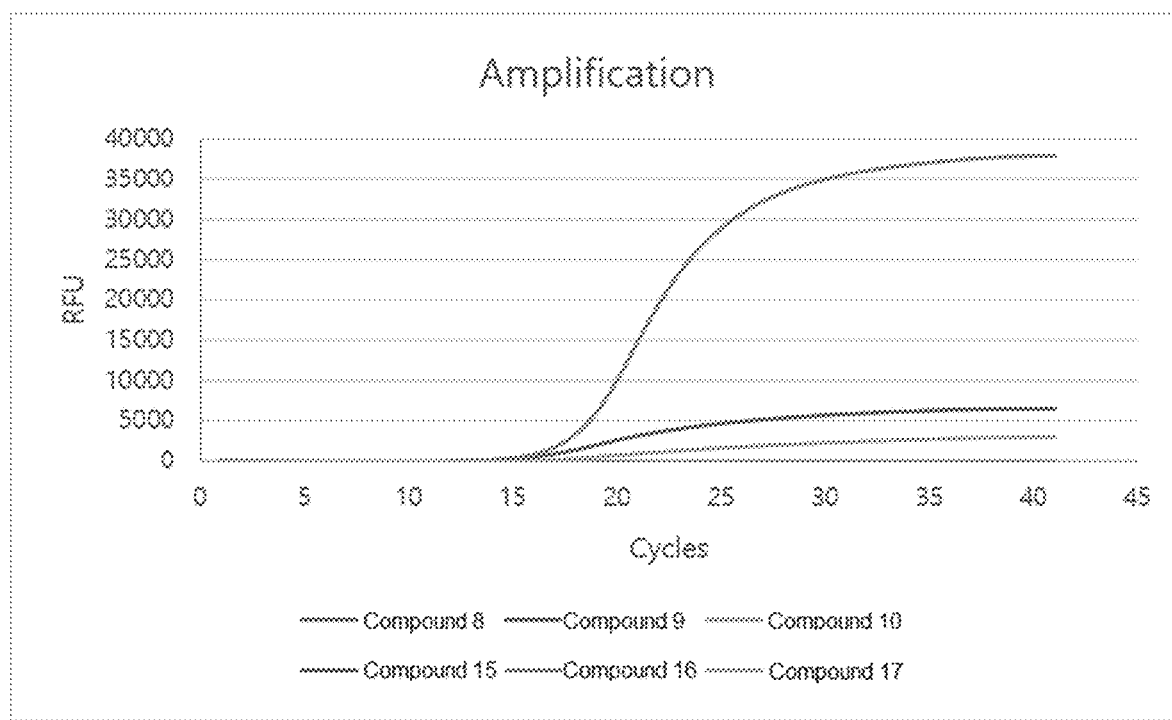
FIG. 1 illustrates a fluorescence intensity shown when DNA is synthesized using a fluorescent compound in accordance with exemplary embodiments of the present invention.

Hereinafter, a preparation method of a fluorescent compound in accordance with exemplary embodiments of the present invention and the fluorescence efficiency and the like of the compound will be described in detail using Examples of the present invention.

Exemplary embodiments of the present invention provide a compound represented by the following Chemical Formula 1.

[Chemical Formula 1]

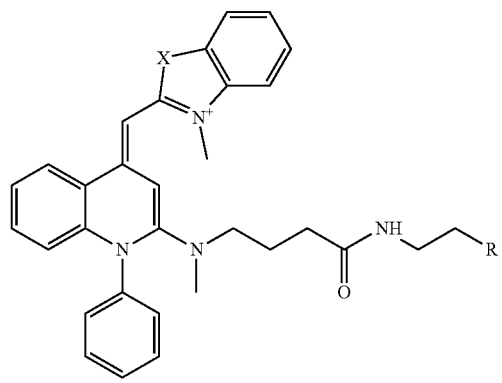

Wherein,

X is oxygen or sulfur, and

R is —SO$_2$CH(CH$_2$), —CH$_2$N(CH$_3$)$_2$, or unsubstituted alkyl having 5 to 10 carbon atoms.

Specific compounds included in exemplary embodiments of the present invention may be compounds of Compound 8, Compound 9, Compound 10, Compound 15, Compound 16, and Compound 17 below.

Compound 8

Compound 9

Compound 10

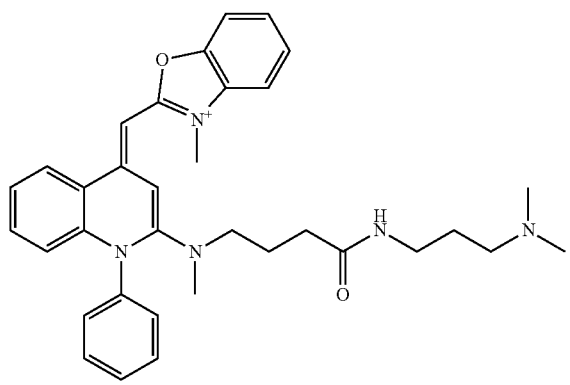

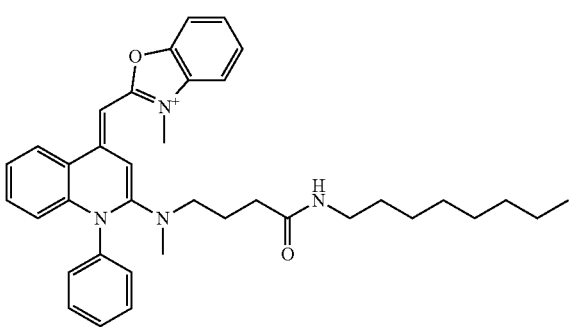

Compound 15

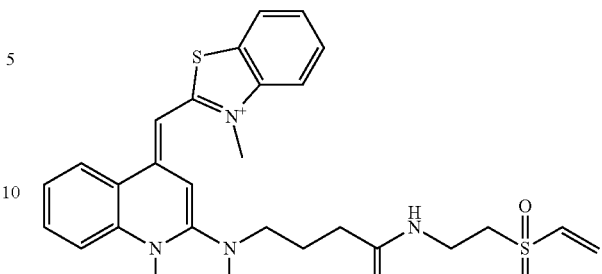

Compound 16

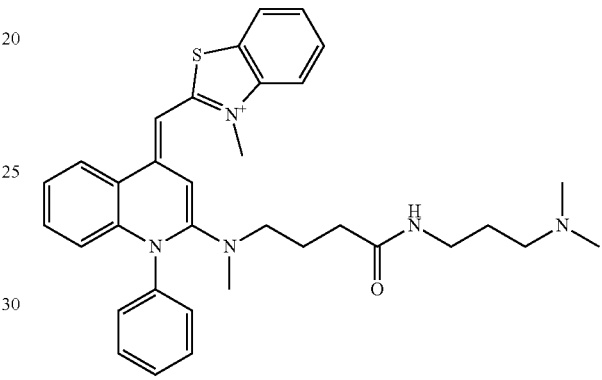

Compound 17

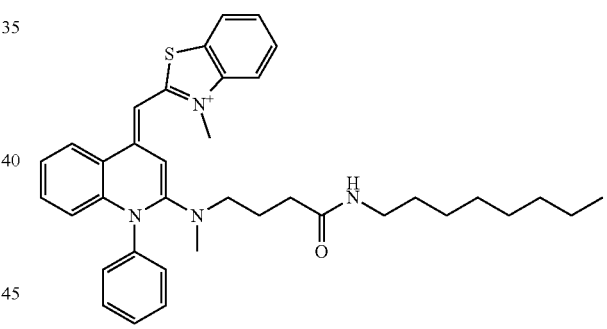

Hereinafter, exemplary embodiments of the present invention will be described in more detail through Examples. However, the following Examples are not to limit the scope of the present invention and will be described to help in the understanding of the present invention.

A preparation method of a compound in accordance with exemplary embodiments of the present invention is as follows.

Compound 1

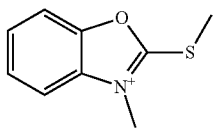

2-(methylthio)benzoxazole (5 ml, 37.5 mmol) and methyl p-toluensulfonate (11.3 ml, 75.1 mmol) were dissolved in 5 ml of dimethylformamide, and then stirred at 150° C. for 1 hour under a nitrogen atmosphere. After the reaction was completed, particles were precipitated with ethylacetate, separated using a centrifuge, and then dried in a vacuum dryer to obtain Compound 1 above.

LC/MS, calculated value of $C_9H_{10}NOS^+$ 180.2, measured value of 180.1

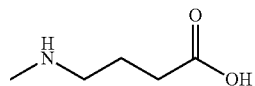

Compound 2

1-methyl-2-pyrroldinone (50 ml, 0.520 mol) was dissolved in 80 ml of hydrochloride, and then stirred at 130° C. for 12 hours under a nitrogen atmosphere. After the reaction was completed, particles were precipitated using 500 ml of acetone after drying under reduced pressure. The precipitated particles were filtered under reduced pressure and then dried to obtain Compound 2 above.

LC/MS, calculated value of $C_5H_{11}NO_2$ 117.1, measured value of 118.1

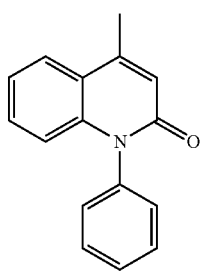

Compound 3

4-methyl carbostyril (10 g, 32.9 mmol), copper powder (24 g, 37.7 mmol), and potassium carbonate (8.7 g, 62.9 mmol) were dissolved in 80 ml of Iodobenzene and then stirred at 200° C. for 48 hours under a nitrogen atmosphere. After the reaction was completed, the mixture was extracted 3 times with ethylacetate and distilled water. An organic layer was collected, concentrated after removing moisture with magnesium sulfate, and then purified by silica gel chromatography (eluent: 50 to 100% EA-Hexane) to obtain Compound 3 above.

LC/MS, calculated value of $C_{16}H_{13}NO$ 235.2, measured value of 236.3

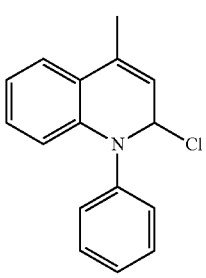

Compound 4

Phosphorus(V) oxychloride (187 μl, 2 mmol) was dissolved in 100 μl of dimethylformamide in an ice bath, Compound 3 was dissolved in 3.5 ml of dichloromethane, added to the reaction solution, and then stirred at 60° C. for 24 hours under a nitrogen atmosphere to obtain Compound 4 above.

LC/MS, calculated value of $C_{16}H_{14}ClN$ 255.7, measured value of 254.1

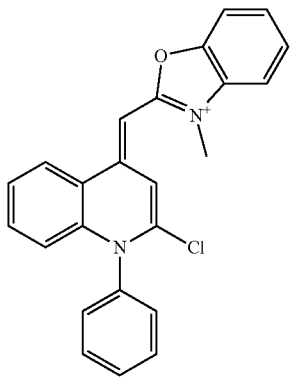

Compound 5

Compound 1 (360 mg, 2 mmol) and triethylamine (1.3 ml, 10 mmol) were added to the reaction solution of Compound 4 and then stirred at 60° C. for 2 hours. After cooling to room temperature, particles were precipitated with diethyl ether, and then separated using a centrifuge. The separated particles were purified by silica gel chromatography (eluent: DCM:MeOH:EA=4:1:3) to obtain Compound 5 above.

LC/MS, calculated value of $C_{24}H_{18}ClN_2O^+$ 385.8, measured value of 385.1

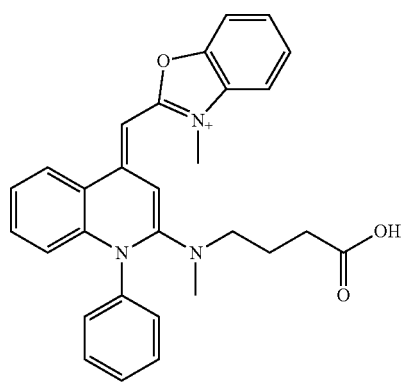

Compound 6

Compound 2 (292 mg, 2.49 mmol) and t-butylmethylsilyl chloride (311 mg, 2.07 mmol) were dissolved in 20 ml of 1,2-dichloroethane, and then added with triethylamine (1.34 ml, 9.62 mmol) and stirred at room temperature for 4 hours. Compound 5 (275 mg, 0.711 mmol) was added to the reaction solution, and then stirred at 60° C. for 1 hour under a nitrogen atmosphere. After cooling to room temperature, particles were precipitated with diethyl ether, separated using a centrifuge, and then dried to obtain Compound 6 above.

LC/MS, calculated value of $C_{29}H_{28}N_3O_3^+$ 466.5, measured value of 466.2

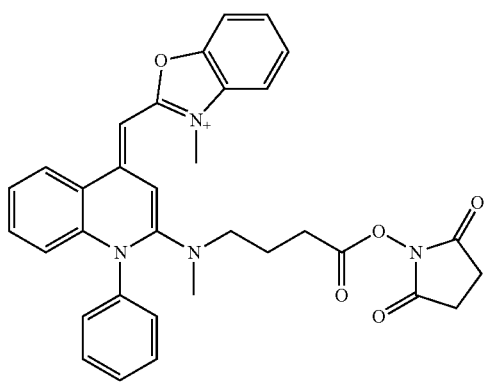

Compound 7

Compound 6 (70 mg, 0.15 mmol) and N,N,N',N'-tetramethyl-O—(N-succinimidyl)uronium tetrafluoroborate (45.2 mg, 0.15 mmol) were dissolved in 4 ml of dimethylformamide, and then added with triethylamine (104.5 µl, 0.75 mmol) and stirred at room temperature for 30 minutes. Particles were precipitated with diethyl ether, separated using a centrifuge, and then dried to obtain Compound 7 above.

LC/MS, measured value of $C_{33}H_{31}N_4O_5^+$ 563.6, measured value of 563.3

Compound 8

Compound 7 (178 mg, 0.317 mmol) and 2-(2-chloroethylsulfonyl)ethanamine hydrochloride (132 mg, 0.634 mmol) were dissolved in 5 ml of dimethylformamide, and then added with N,N-diisopropylethylamine (552 µl, 3.17 mmol) and stirred for 24 hours at room temperature. Particles were precipitated with diethyl ether, separated using a centrifuge, and then dried to obtain Compound 8 above.

LC/MS, calculated value of $C_{33}H_{35}N_4O_4S^+$ 583.7, measured value of 583.3

Compound 9

Compound 7 (207 mg, 0.367 mmol) and 3-(dimethylamino)-1-propylamine (139 µl, 1.10 mmol) were dissolved in 5 ml of dimethylformamide, and then added with N,N-diisopropylethylamine (639 µl, 3.67 mmol) and stirred for 24 hours at room temperature. Particles were precipitated with diethyl ether, separated using a centrifuge, and then dried to obtain Compound 9 above.

LC/MS, calculated value of $C_{34}H_{40}N_5O_2^+$ 550.7, measured value of 550.4

Compound 10

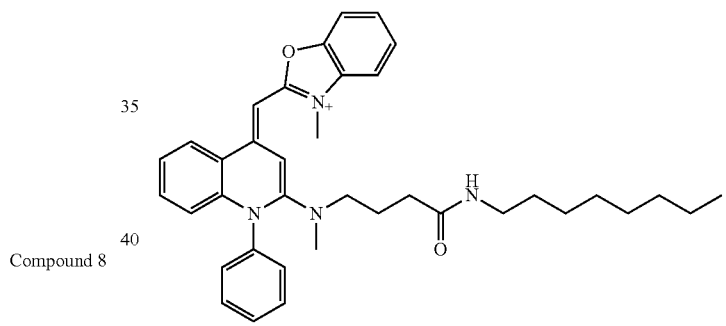

Compound 7 (247 mg, 0.438 mmol) and octylamine (217 µl, 1.31 mmol) were dissolved in 5 ml of dimethylformamide, and then added with N,N-diisopropylethylamine (762 µl, 4.38 mmol) and stirred for 24 hours at room temperature. Particles were precipitated with diethyl ether, separated using a centrifuge, and then dried to obtain Compound 10 above.

LC/MS, calculated value of $C_{37}H_{45}N_4O_2^+$ 577.7, measured value of 577.4

Compound 11

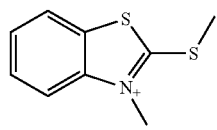

2-(methylthio)benzoxazole (5 g, 0.028 mol) and iodomethane (6.9 ml, 0.110 mol) were dissolved in 20 ml of methanol, and then stirred at 50° C. for 24 hour under a nitrogen atmosphere. After the reaction was completed, the reaction solution was dried under reduced pressure, and then particles were precipitated with diethyl ether. The precipitated particles were filtered under reduced pressure and then dried in vacuum to obtain Compound 11 above.

LC/MS, calculated value of $C_9H_{10}NS_2^+$ 196.3, measured value of 196.2

Compound 12

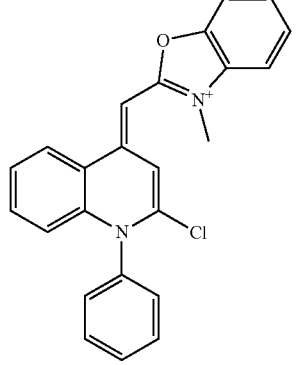

Compound 11 (392 mg, 2 mmol) and triethylamine (0.28 ml, 2 mmol) were added to the reaction solution of Compound and then stirred at room temperature for 12 hours. Particles were precipitated with diethyl ether, and then separated using a centrifuge. The separated particles were purified by silica gel chromatography (eluent: $CHCl_3$: MeOH:EA=3:1:3) to obtain Compound 12 above.

LC/MS, calculated value of $C_{24}H_{18}ClN_2S^+$ 401.9, measured value of 401.1

Compound 13

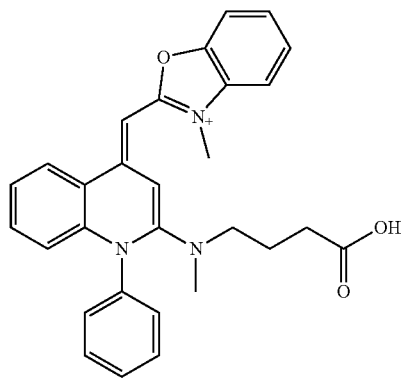

Except for using Compound 12 instead of Compound 5, Compound 13 above was obtained through the same process as the method of synthesizing Compound 6.

LC/MS, calculated value of $C_{29}H_{28}N_3O_2S^+$ 482.6, measured value of 482.2

Compound 14

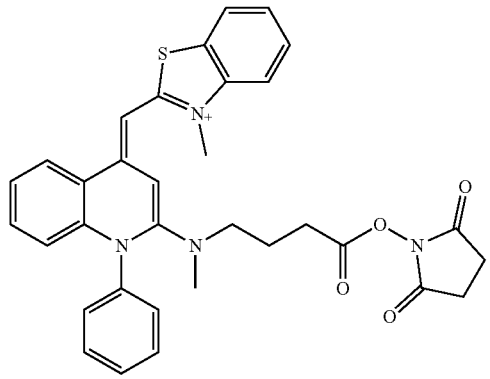

Compound 14

Except for using Compound 13 instead of Compound 6, Compound 14 above was obtained through the same process as the method of synthesizing Compound 7.

LC/MS, calculated value of $C_{33}H_{31}N_4O_4S^+$ 579.6, measured value of 579.2

Compound 15

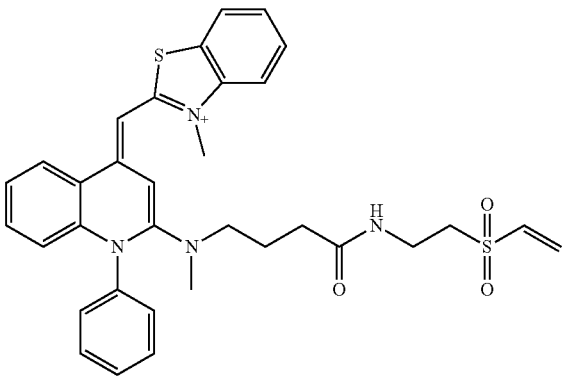

Except for using Compound 14 instead of Compound 7, Compound 15 above was obtained through the same process as the method of synthesizing Compound 8.

LC/MS, calculated value of $C_{33}H_{35}N_4O_3S_2^+$ 599.7, measured value of 599.3

Compound 16

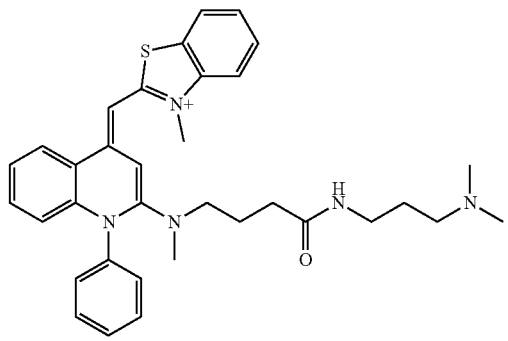

Except for using Compound 14 instead of Compound 7, Compound 16 above was obtained through the same process as the method of synthesizing Compound 9.

LC/MS, calculated value of $C_{34}H_{40}N_5OS^+$ 566.7, measured value of 566.9

Compound 17

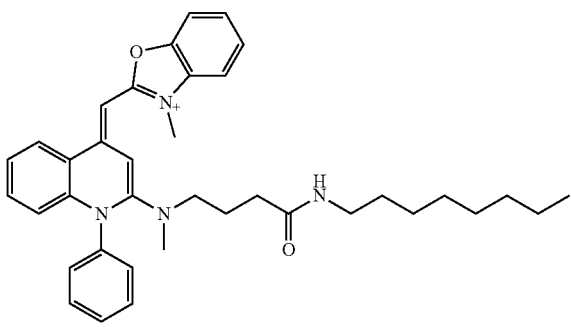

Except for using Compound 14 instead of Compound 7, Compound 17 above was obtained through the same process as the method of synthesizing Compound 10.

LC/MS, calculated value of $C_{37}H_{45}N_4OS^+$ 593.8, measured value of 594.0

Examples: Preparation of Contrast Agent Composition Using Compound of the Present Invention (1) Preparation of Reagent for Real-Time PCR Analysis Compounds 8, 9, 10, 15, 16, and 17 were dissolved in dimethyl sulfoxide to prepare 5 mM of a stock solution. The prepared stock solution was diluted in a Tris-EDTA buffer (pH 7.5) and prepared at a concentration of 200 uM.

For Reference material 1, 10,000× of the stock solution was diluted to a concentration of 20× through a Tris-EDTA buffer (pH 7.5). For Reference material 2, 20,000× of the stock solution was diluted to a concentration of 20× through a Tris-EDTA buffer (pH 7.5).

(2) Compound Analysis Through Real-Time RCR

Reference materials 1 (Evagreen) and 2 (Invitrogen Sybr Green) and Compounds 8, 9, 10, 15, 16, and 17 were compared and verified by an intercalating method using a double-stranded DNA binding dyes through real-time PCR. cDNA extracted from HeLa cells was used, and b-actin (Forward 5'-CAT CGA GCA CGG CAT CGT CA-3', Reverse 5'-TAG CAC AGC CTG GAT AGC AAC-3') was used as a primer. Real-time PCR reaction was performed using a CFX96 touch real-time PCR detection system (BIO-RAD). The PCR mixture consisted of a total 20 uL of reaction solution containing 1 uL of a forward primer, 1 uL of a reverse primer, 10 uL of a PCR master mix (TAKARA), 1 uL of a reference material and each compound (Compounds 8, 9, 10, 15, 16, 17), and 1 uL of template cDNA. PCR conditions were as follows: (a) In a pre-denaturing step, 1 minute at 95° C. (b) 45 cycles are configured as a cycle consisting of at 95° C. for 15 seconds, 58° C. for 30 seconds and 72° C. for 30 seconds, and a fluorescence wavelength of 497 nm was detected in a cycle of 30 seconds at 72° C.

FIG. 1 illustrates that fluorescence signals were not strongly observed during DNA synthesis using Compounds 8, 9, and 10, and the $C_q$ values were not much confirmed as in FIG. 3. On the other hand, it can be seen that Compounds 15, 16, and 17 emit visible fluorescence by binding to DNA during DNA amplification as illustrated in FIG. 1. Compounds 15 and 17 were not much strong in fluorescence, and the $C_q$ value of Compound 17 was also hardly confirmed. On the other hand, it can be seen that Compound 16 shows a very strong fluorescence intensity and the $C_q$ value is also the fastest.

Figure 2:
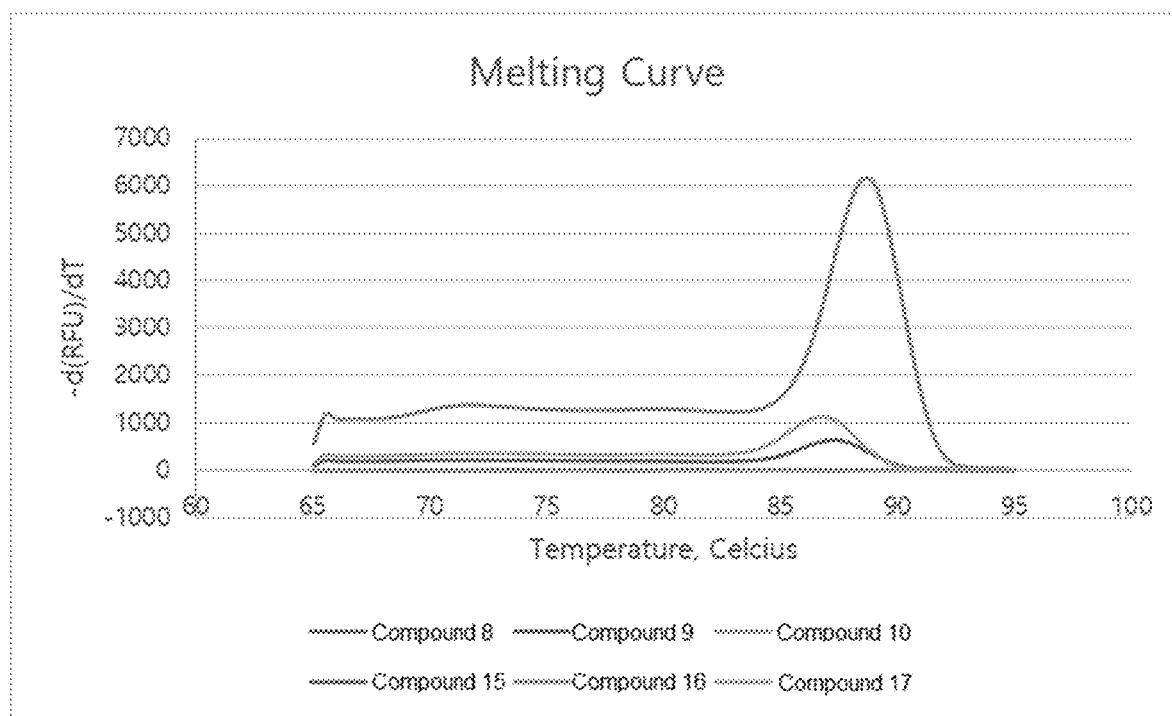
FIG. 2 illustrates a melting curve shown when DNA is synthesized using the fluorescent compound in accordance with exemplary embodiments of the present invention.

FIG. 2 shows a melting curve and shows the same result as the above result.

Figure 4:
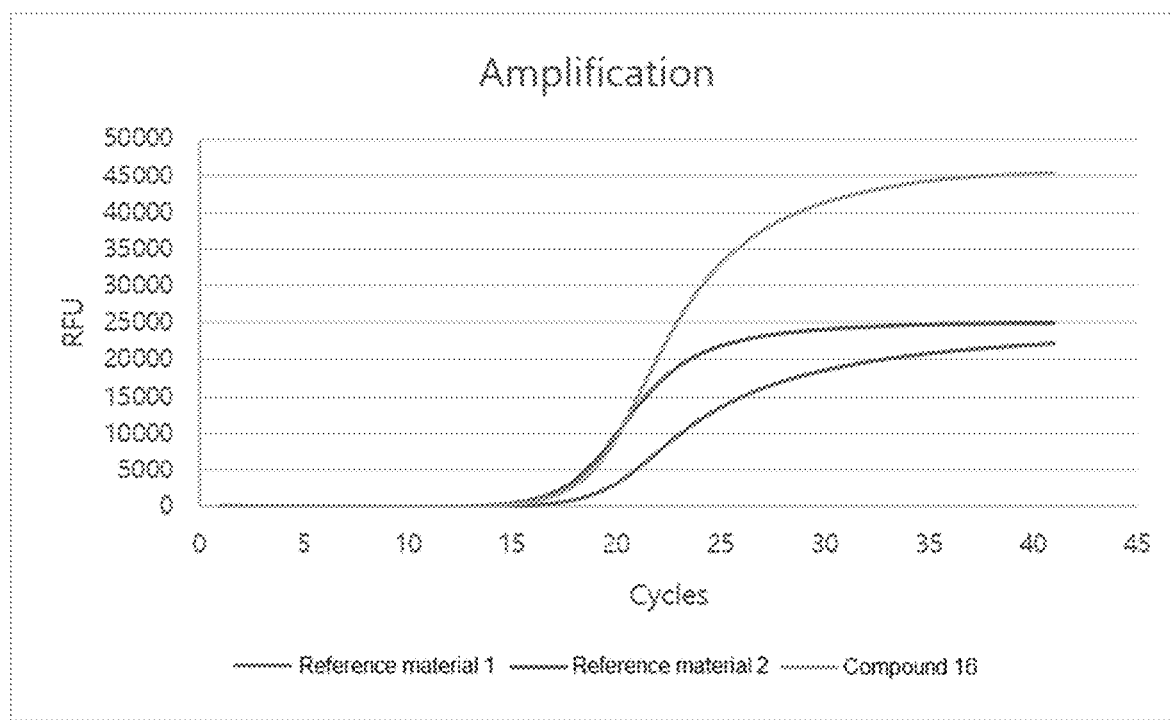
FIG. 4 illustrates comparison of fluorescence intensities shown when DNA is synthesized using a fluorescent compound of embodiments of the present invention and a reference material.

As illustrated in FIG. 4, Compound 16 showed a fluorescence intensity that was two times higher than that of Reference materials 1 and 2, and a $C_q$ value that was faster than that of Reference material 1 was confirmed.

Figure 5:
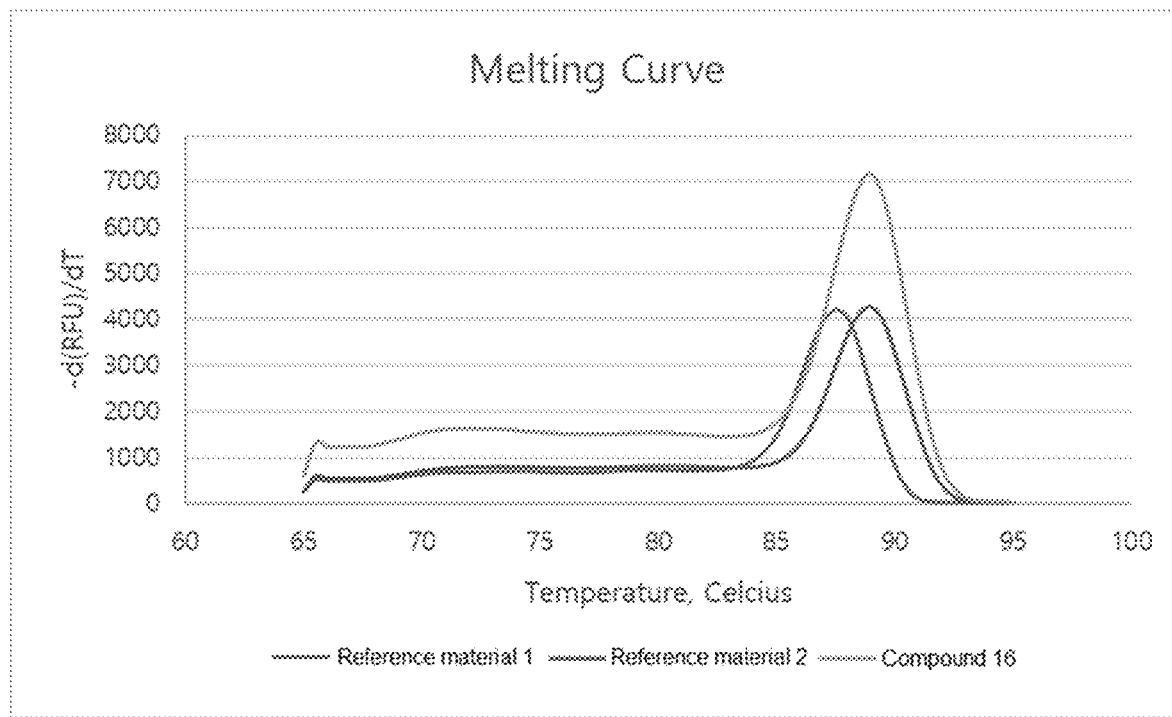
FIG. 5 illustrates a difference in melting curve shown when DNA is synthesized using a fluorescent compound of embodiments of the present invention and a reference material.
Figure 7:
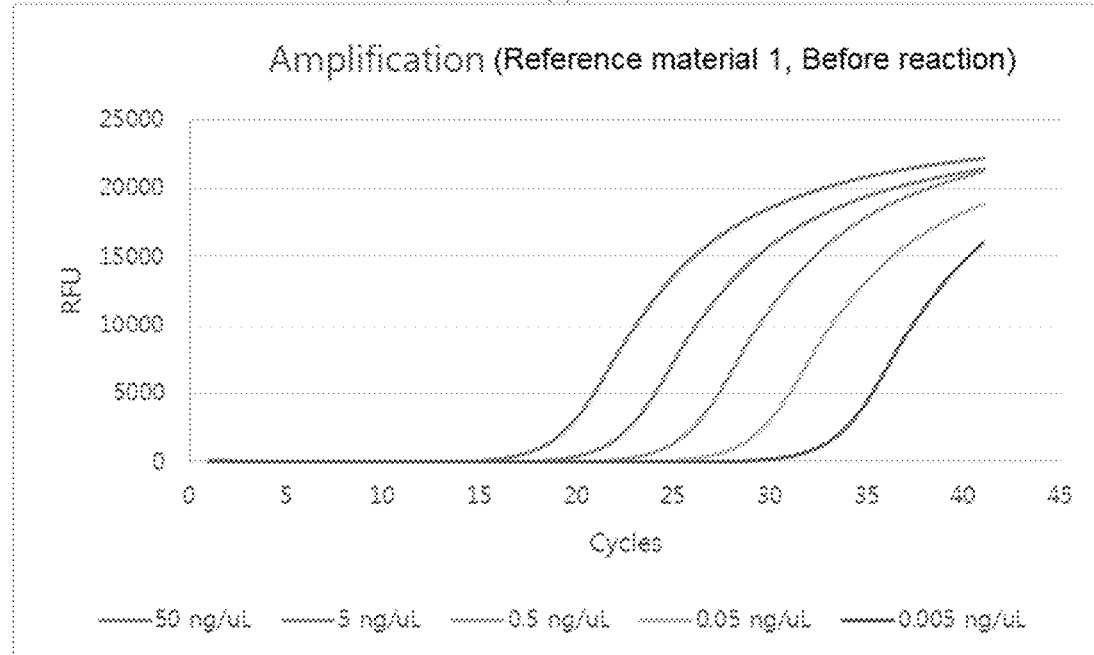
FIG. 7 illustrates changes in fluorescence intensity according to concentrations of a compound of embodiments of the present invention and a reference material before reaction when DNA is synthesized using the compound of embodiments of the present invention and the reference material.
Figure 7:
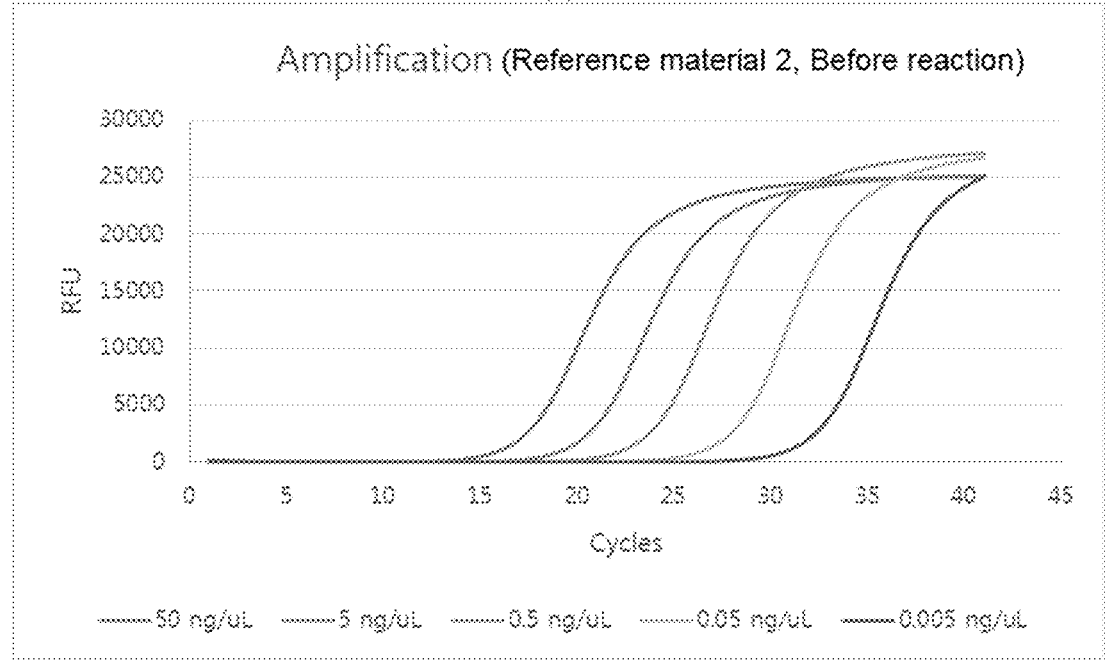
Figure 7:
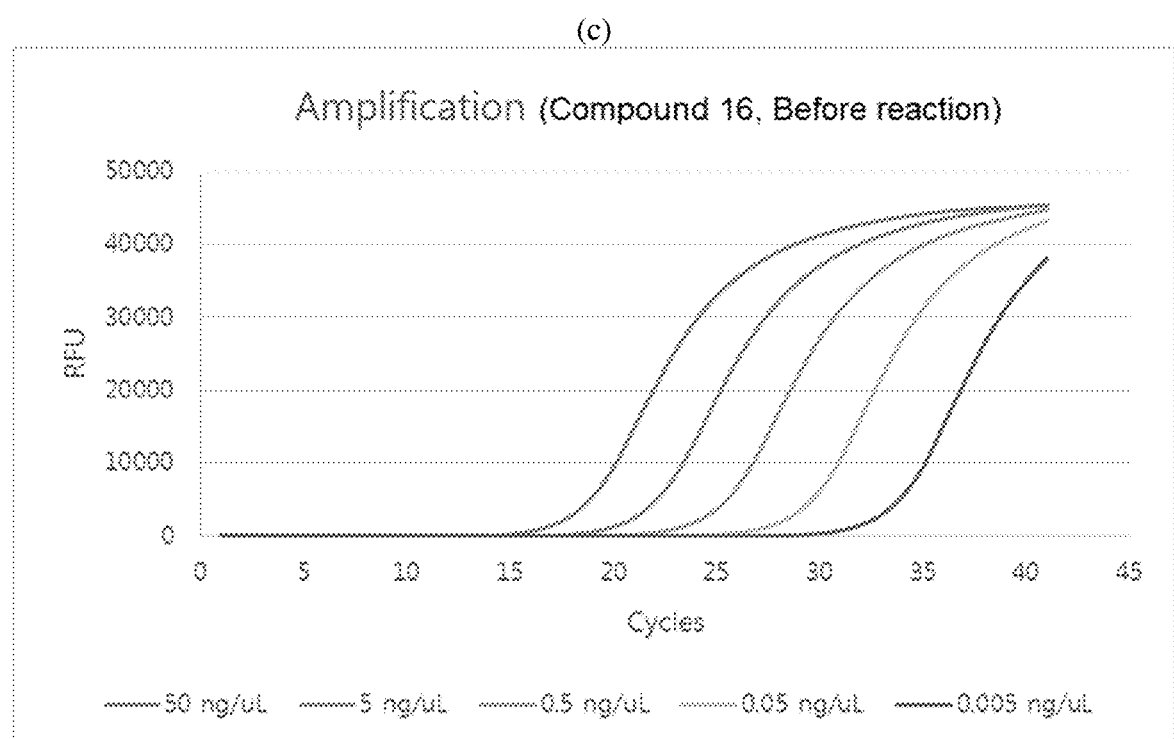
Figure 8:
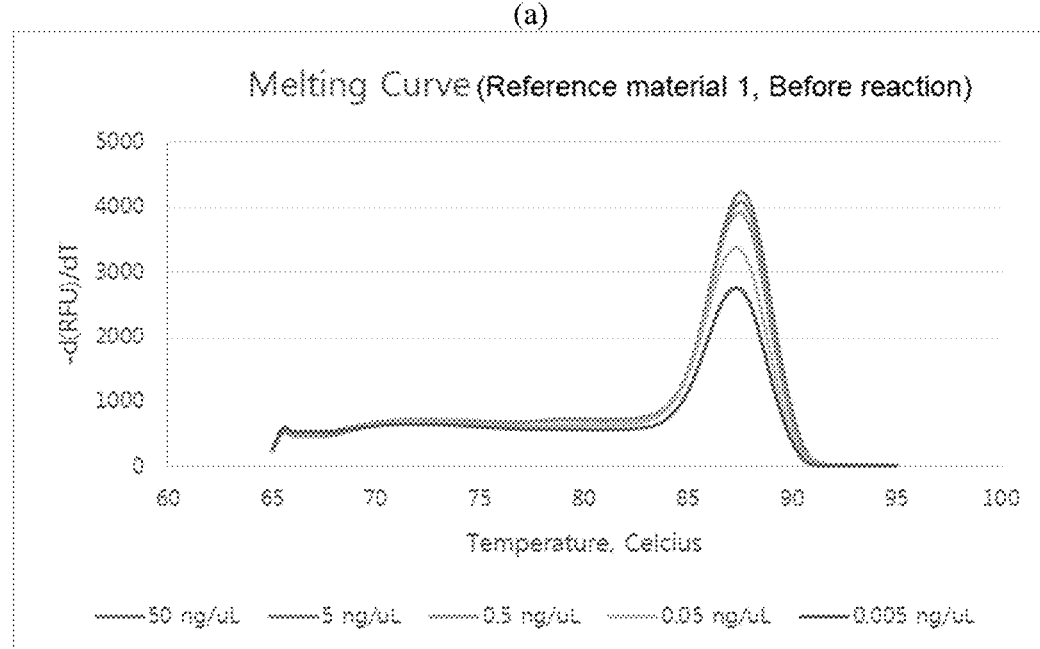
FIG. 8 illustrates changes in melting curve according to concentrations of the compound of embodiments of the present invention and the reference material before reaction when DNA is synthesized using the compound of embodiments of the present invention and the reference material.
Figure 8:
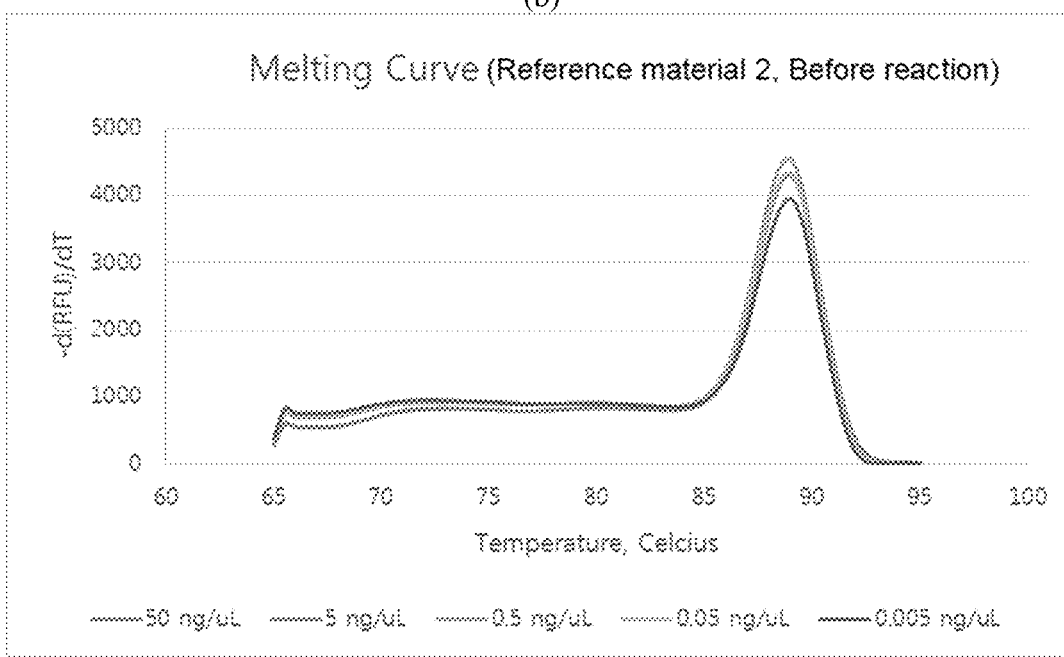
Figure 8:
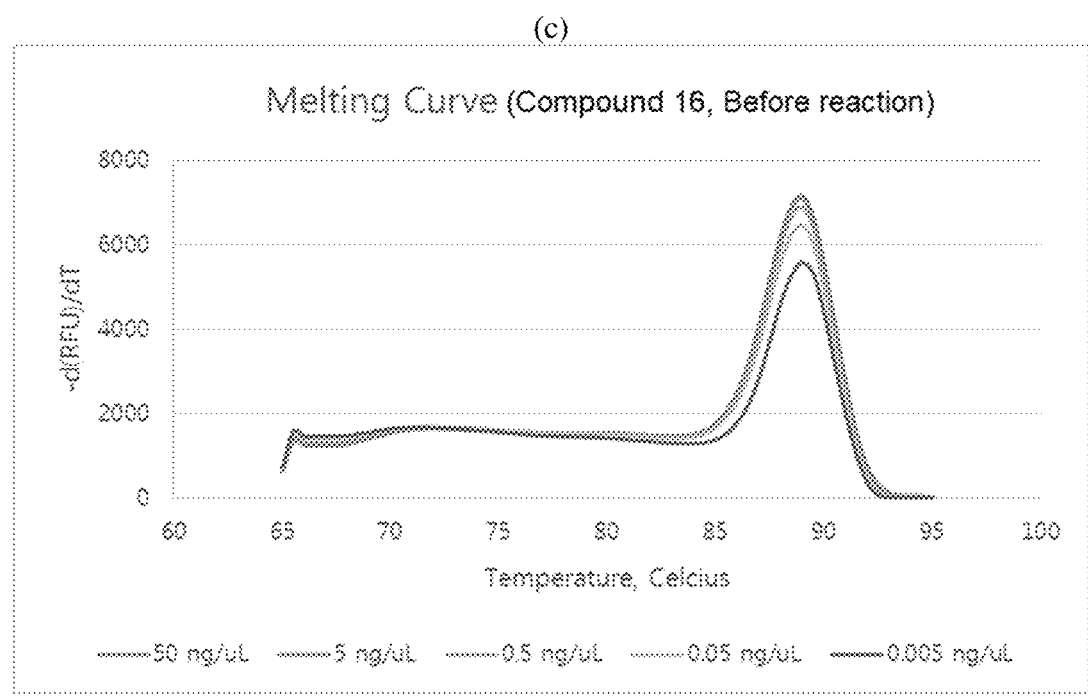
Figure 10:
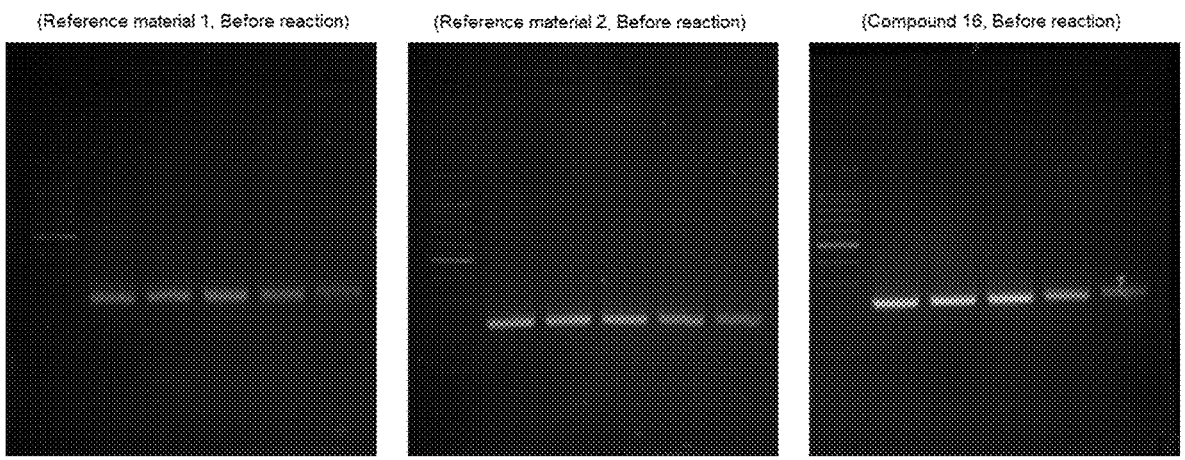
FIG. 10 illustrates electrophoresis results before reaction when DNA is synthesized using the compound of embodiments of the present invention and the reference material.
Figure 11:
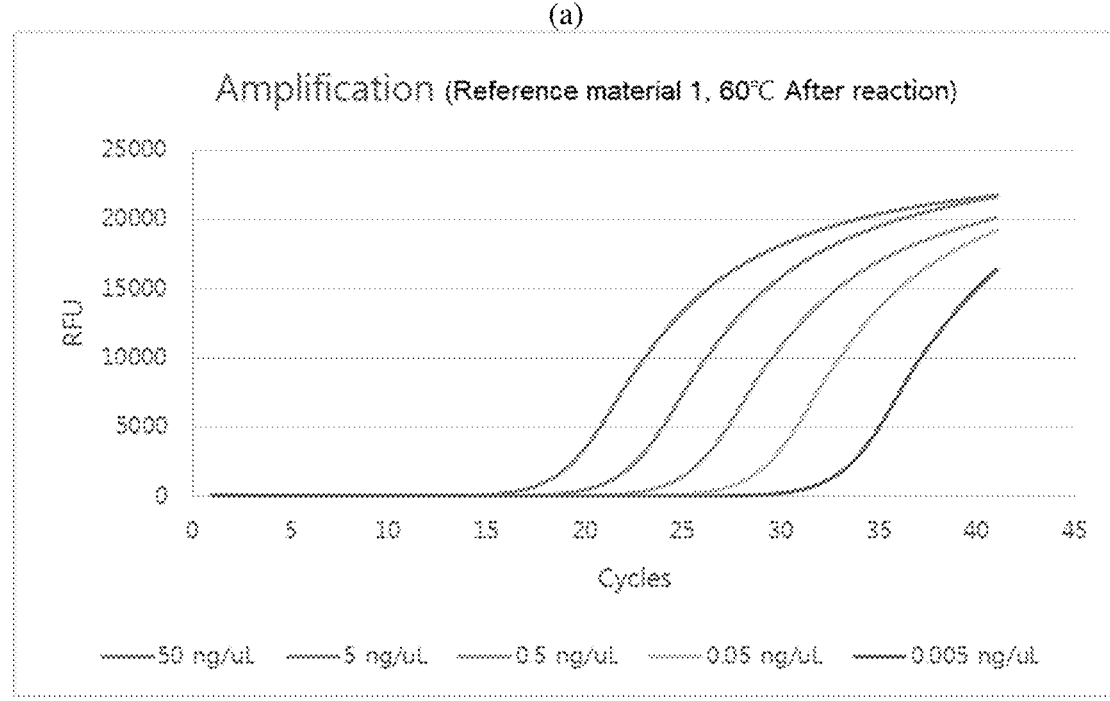
FIG. 11 illustrates changes in fluorescence intensity according to concentrations of a compound of embodiments of the present invention and a reference material after reaction when DNA is synthesized using the compound of embodiments of the present invention and the reference material.
Figure 11:
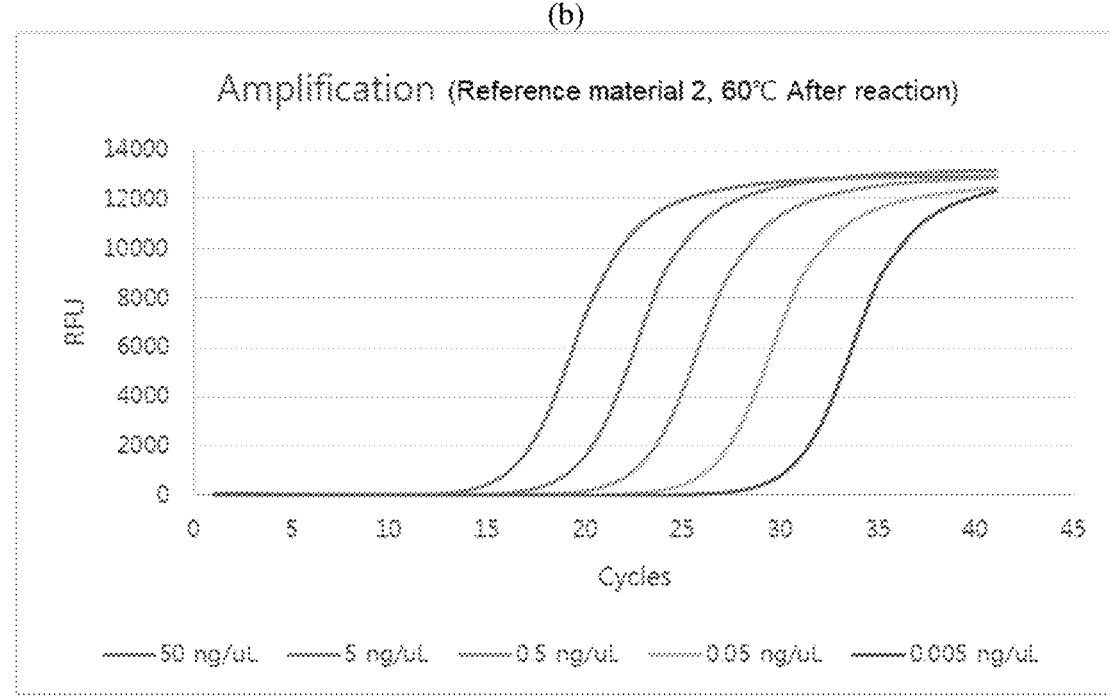
Figure 11:
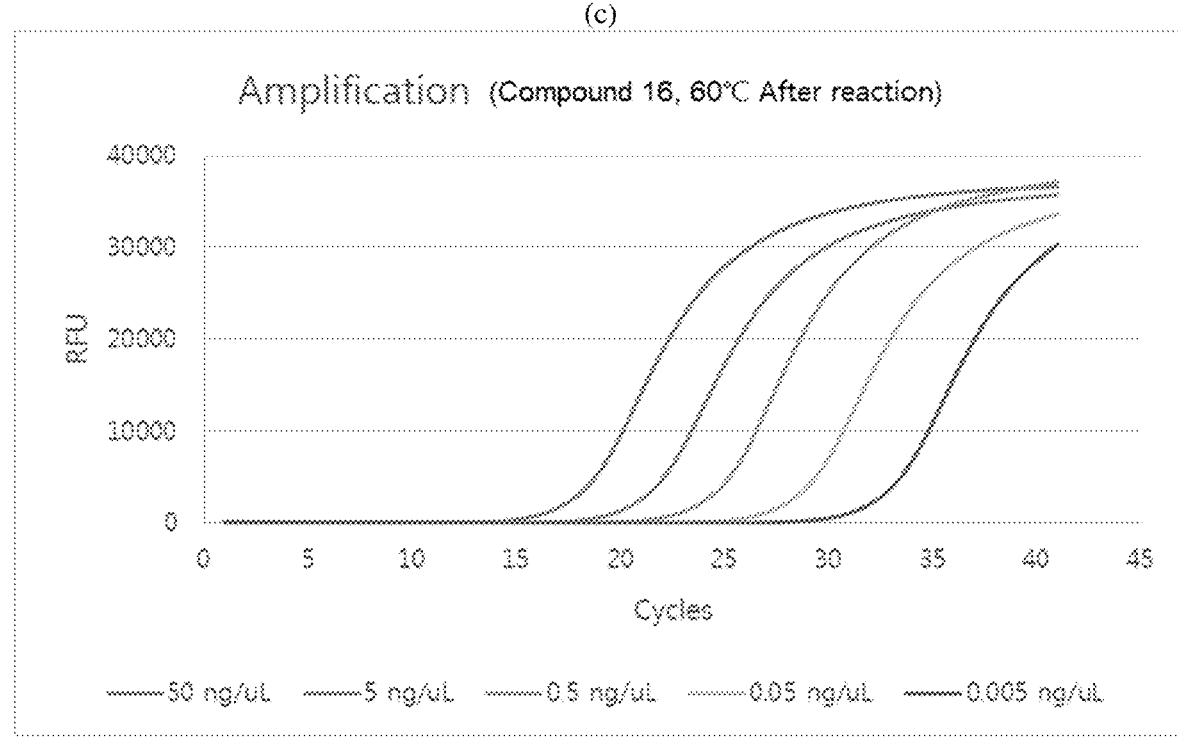
Figure 12:
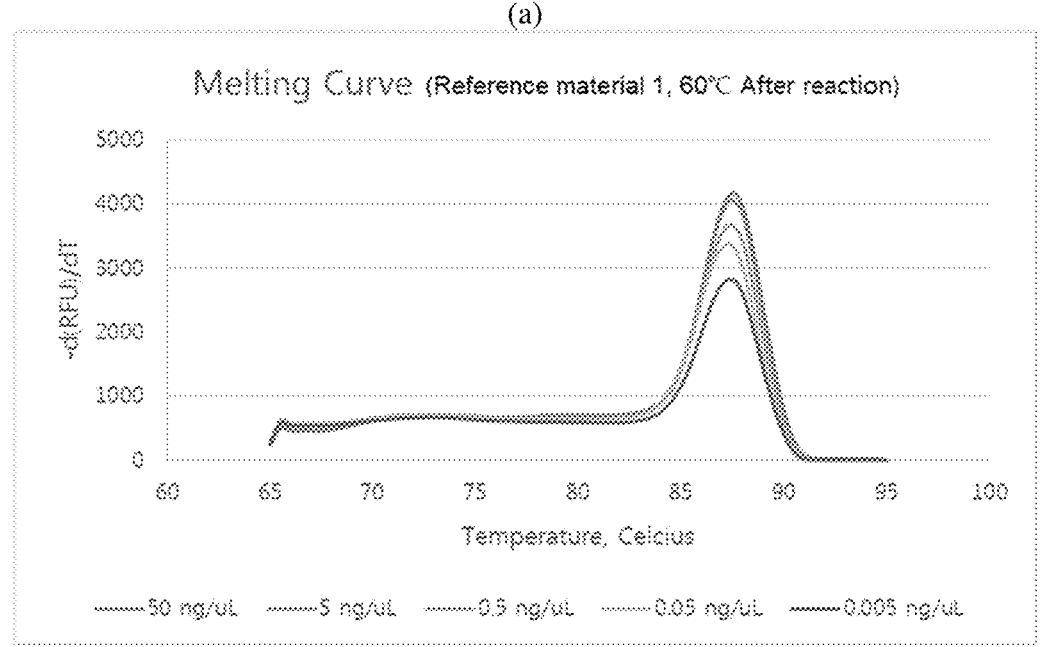
FIG. 12 illustrates changes in melting curve according to concentrations of a compound of embodiments of the present invention and a reference material after reaction when DNA is synthesized using the compound of embodiments of the present invention and the reference material.
Figure 12:
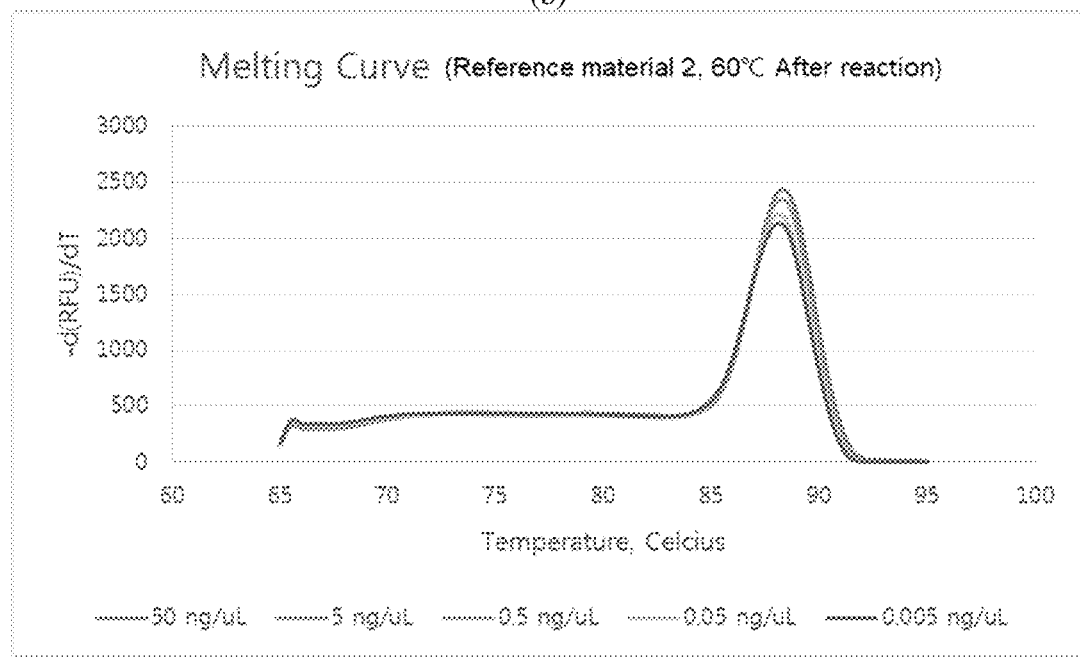
Figure 12:
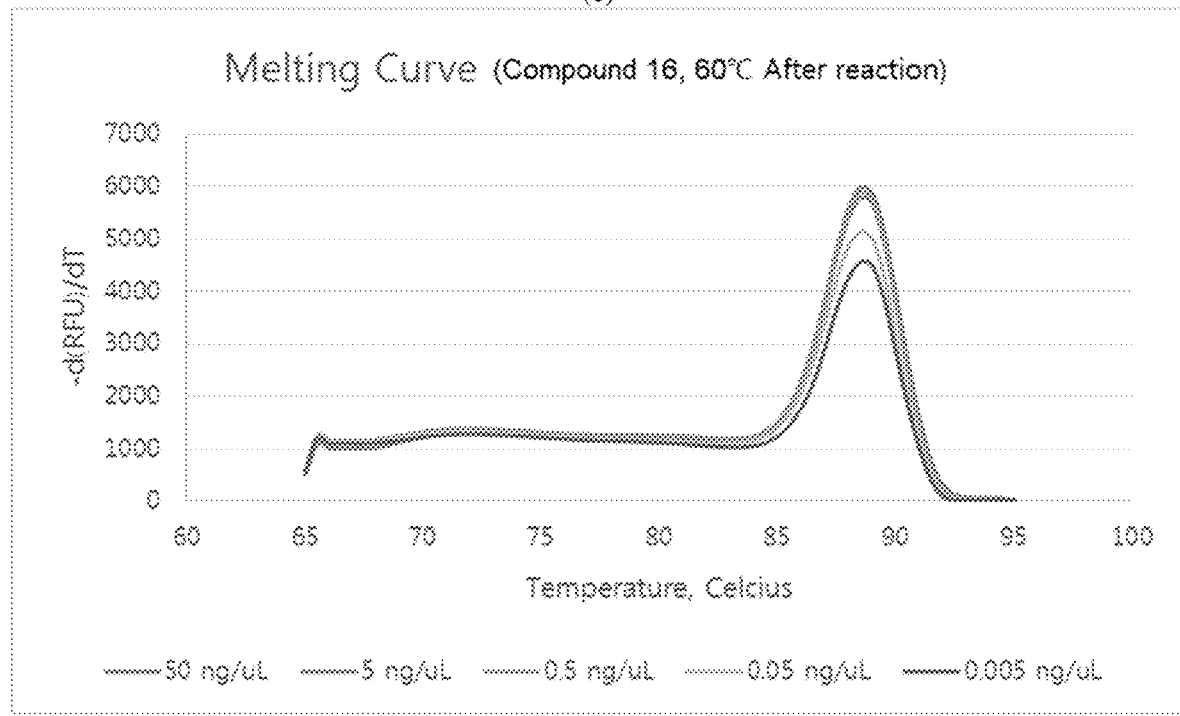
Figure 14:
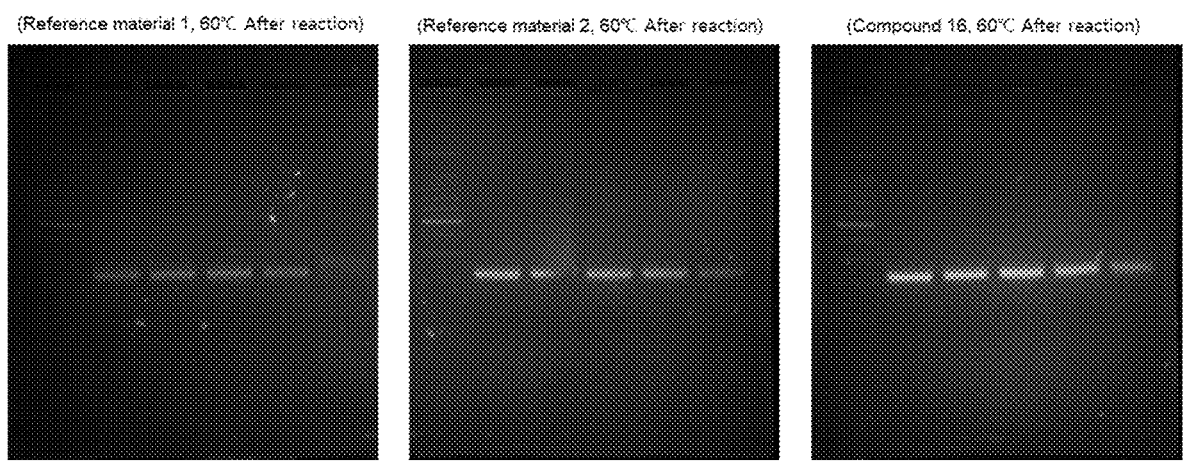
FIG. 14 illustrates electrophoresis results after reaction when DNA is synthesized using the compound of embodiments of the present invention and the reference material.

FIG. 5 shows a melting curve and shows the same result as the above result.

(3) Stability Analysis of Compound

Stability analysis was performed by storing Reference materials 1 (Evagreen) and 2 (Invitrogen Sybr Green) and Compound 16 in an incubator at 60° C. The three materials were stored in an incubator at 60° C. for 3 days, and the fluorescence signals for each template concentration were analyzed by real-time PCR analysis as in (1) above, and the PCR product was electrophoresed to analyze whether normal DNA synthesis was achieved. After real-time-PCR, synthetic DNA and a 6× Loading dye (BioActs) were mixed, and then electrophoresis was performed for 35 minutes on a 2% agarose gel (Simga-aldrich).

FIGS. 7, 8, 9, and 10 illustrate real-time PCR and electrophoresis results before reaction at 60° C.

FIGS. 11, 12, 13, and 14 showed no significant change in Reference material 1 and Compound 16 as a result of reaction at 60° C. for 3 days. On the other hand, it was confirmed that the fluorescence intensity of Reference material 2 decreased by about half, and Compound 16 was a more stable material than Reference material 2. In addition, as a result of electrophoresis, Compound 16 showed clearer DNA synthesis results than Reference materials 1 and 2.

From the results, it can be seen that the compounds provided by the present invention have effects on the DNA synthetic fluorescent dye less than the conventional fluorescent compounds, and thus, the compounds have excellent stability.

The present invention is not limited by the above-described embodiments, and various modifications and changes can be made by those skilled in the art and may be used in various biological and chemical fields, and are included in the spirit and scope of the present invention as defined in the appended claims.

What is claimed is:

1. An intercalating dye compound for analyzing biomaterials, wherein the compound is a compound represented by the following Chemical Formula 1 or a salt thereof;

[Chemical Formula 1]

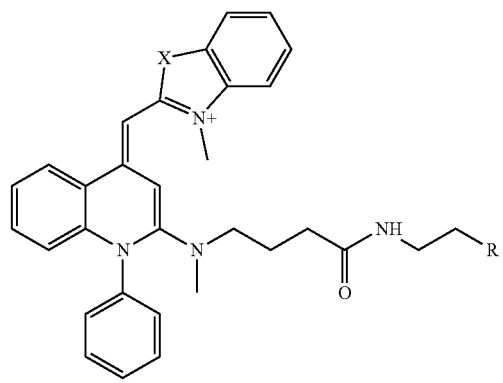

Wherein,

X is oxygen or sulfur, and

R is —SO$_2$CH(CH$_2$), —CH$_2$N(CH$_3$)$_2$, or unsubstituted alkyl having 5 to 10 carbon atoms.

2. The compound of claim 1, wherein the compound of Chemical Formula 1 is selected from the group consisting of the following Compounds 8, 9, and 10

Compound 8

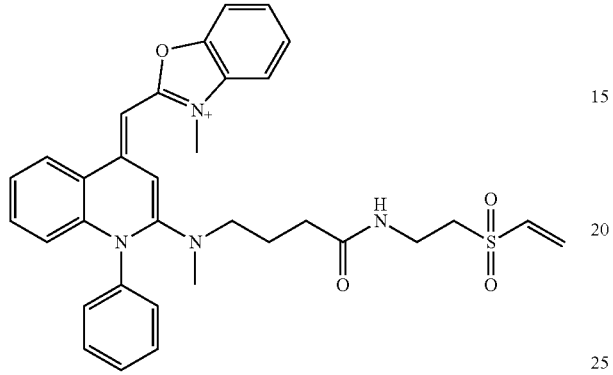

Compound 9

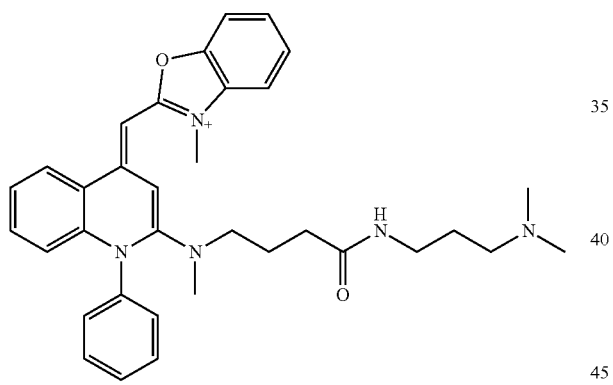

Compound 10

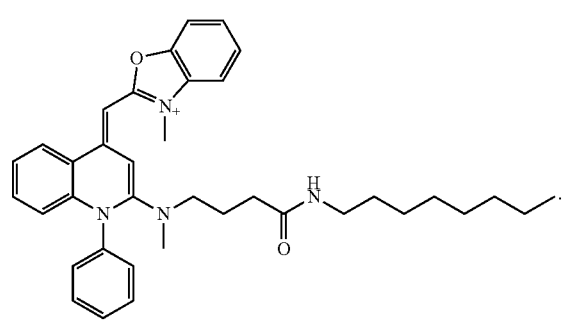

3. The compound of claim 1, wherein the compound of Chemical Formula 1 is selected from the group consisting of the following Compounds 15, 16, and 17

Compound 15

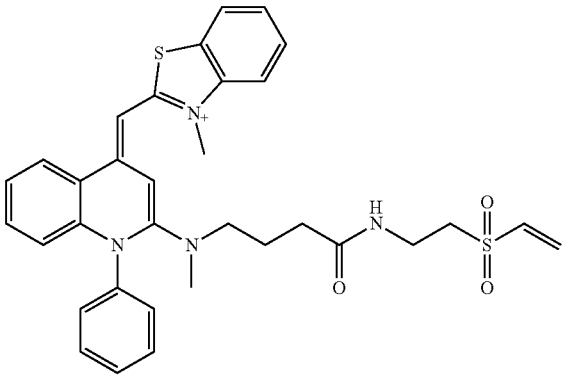

Compound 16

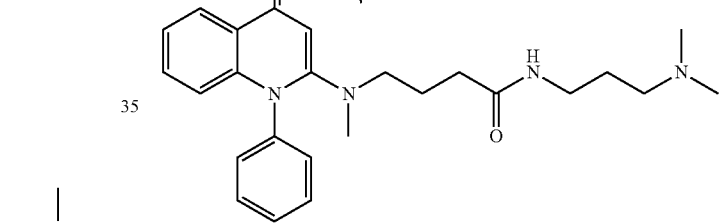

Compound 17

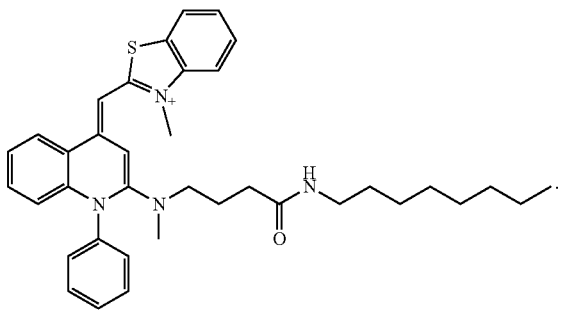

4. The compound of claim 1, wherein the biomaterials are selected from the group consisting of proteins, glycoproteins, siRNA, DNA and RNA.

5. The compound of claim 1, wherein the compound is intercalated between the biomaterials.

6. A contrast agent composition for labeling biomaterials comprising a compound represented by the following Chemical Formula 1 or a salt thereof:

[Chemical Formula 1]

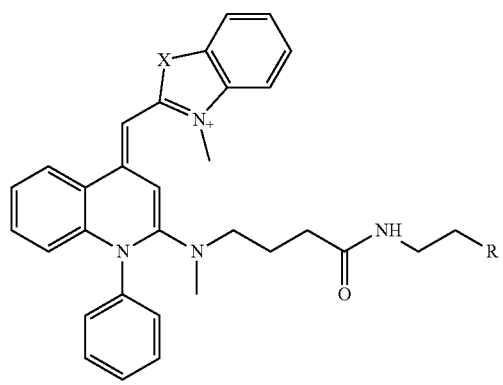

Wherein,

X is oxygen or sulfur, and

R is —SO₂CH(CH₂), —CH₂N(CH₃)₂, or unsubstituted alkyl having 5 to 10 carbon atoms.

7. The contrast agent composition for labeling the biomaterials of claim 6, wherein the compound of Chemical Formula 1 is selected from the group consisting of the following Compounds 8, 9, and 10

Compound 8

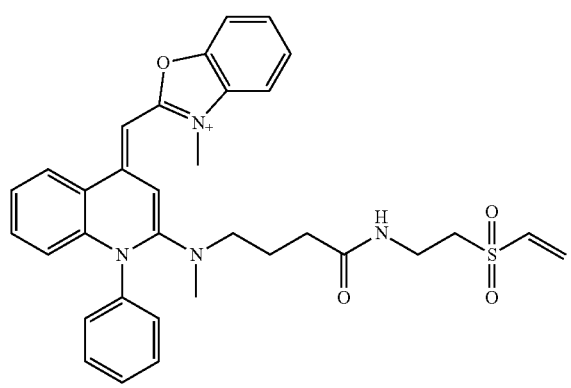

Compound 9

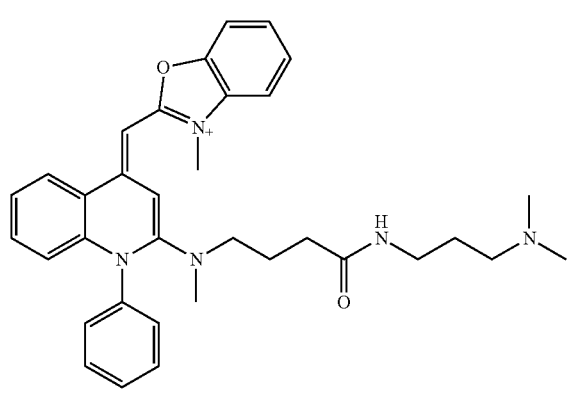

Compound 10

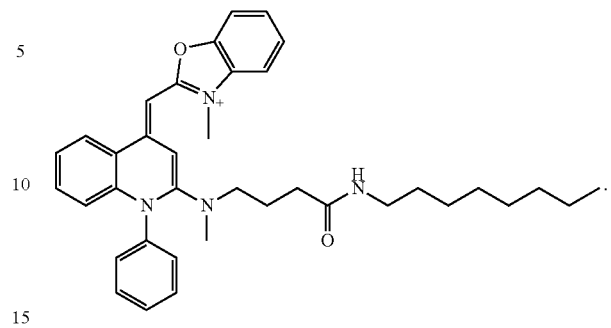

8. The contrast agent composition for labeling the biomaterials of claim 6, wherein the compound of Chemical Formula 1 is selected from the group consisting of the following Compounds 15, 16, and 17

Compound 15

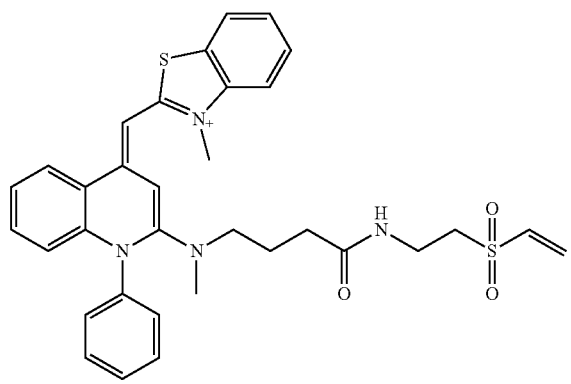

Compound 16

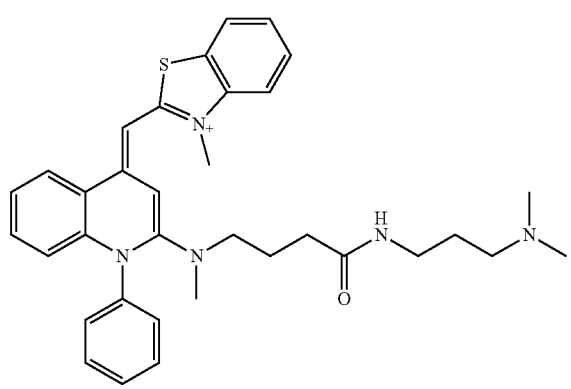

Compound 17

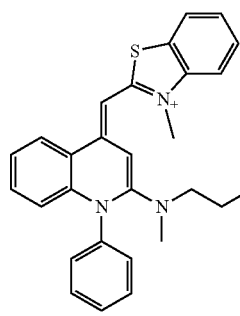

9. The contrast agent composition for labeling the biomaterials of claim 6, wherein the biomaterials are selected from the group consisting of proteins, glycoproteins, siRNA, DNA and RNA.

10. The contrast agent composition for labeling the biomaterials of claim 6, wherein the compound is intercalated between the biomaterials.

11. A kit for detecting biomaterials formed by including a contrast agent composition consisting of a compound represented by the following Chemical Formula 1 or a salt thereof:

[Chemical Formula 1]

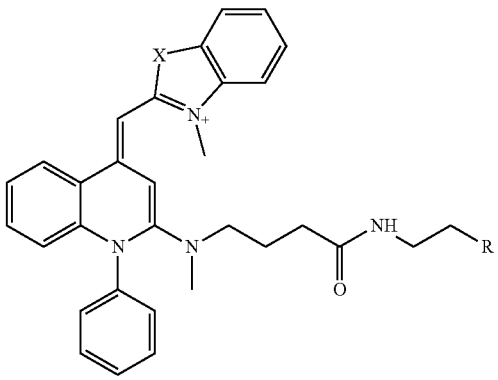

Wherein,
X is oxygen or sulfur, and
R is —$SO_2CH(CH_2)$, —$CH_2N(CH_3)_2$, or unsubstituted alkyl having 5 to 10 carbon atoms.

12. The kit for detecting the biomaterials of claim 11, wherein the biomaterials are selected from the group consisting of proteins, glycoproteins, siRNA, DNA and RNA.

13. The kit for detecting the biomaterials of claim 11, wherein the compound is intercalated between the biomaterials.

* * * * *